United States Patent
Joshi et al.

(10) Patent No.: US 11,352,923 B2
(45) Date of Patent: Jun. 7, 2022

(54) SYSTEM AND METHOD TO MITIGATE SENSOR FAILURES DUE TO WATER CONDENSATION

(71) Applicant: Cummins Inc., Columbus, IN (US)

(72) Inventors: Saurabh Y. Joshi, Indianapolis, IN (US); Neal W. Currier, Columbus, IN (US); Aleksey Yezerets, Columbus, IN (US); Ashok Kumar, Columbus, IN (US); Tyler A. Rash, Columbus, IN (US); Anand Srinivasan, Greenwood, IN (US); Di Wang, Columbus, IN (US); Yadan Tang, Columbus, IN (US)

(73) Assignee: CUMMINS INC., Columbus, IN (US)

( * ) Notice: Subject to any disclaimer, the term of this patent is extended or adjusted under 35 U.S.C. 154(b) by 16 days.

(21) Appl. No.: 16/754,623

(22) PCT Filed: Oct. 10, 2017

(86) PCT No.: PCT/IB2017/056259
§ 371 (c)(1),
(2) Date: Apr. 8, 2020

(87) PCT Pub. No.: WO2019/073280
PCT Pub. Date: Apr. 18, 2019

(65) Prior Publication Data
US 2020/0264147 A1    Aug. 20, 2020

(51) Int. Cl.
*F01N 3/00* (2006.01)
*F01N 3/08* (2006.01)
*F01N 3/20* (2006.01)

(52) U.S. Cl.
CPC .......... *F01N 3/0814* (2013.01); *F01N 3/2066* (2013.01); *F01N 2560/026* (2013.01); *F01N 2560/028* (2013.01); *F01N 2900/1628* (2013.01)

(58) Field of Classification Search
CPC ............ F01N 3/0814; F01N 3/2066; F01N 2900/1628; F01N 2560/026; F01N 2560/028
See application file for complete search history.

(56) References Cited

U.S. PATENT DOCUMENTS

| | | | |
|---|---|---|---|
| 5,590,521 A | * | 1/1997 | Schnaibel ............... F01N 11/00 60/274 |
| 7,654,077 B2 | | 2/2010 | Zillmer et al. |

(Continued)

FOREIGN PATENT DOCUMENTS

| | | |
|---|---|---|
| CN | 101779015 A | 7/2010 |
| CN | 102767437 A | 11/2012 |

(Continued)

OTHER PUBLICATIONS

International Search Report and Written Opinion issued by the ISA/US, Commissioner for Patents, dated Mar. 8, 2018, for PCT/IB2017/056259; 6 pages.

*Primary Examiner* — Matthew T Largi
(74) *Attorney, Agent, or Firm* — Faegre, Drinker, Biddle & Reath, LLP

(57) ABSTRACT

A diagnostic system (10) is provided and includes a sensor (24) disposed downstream from an exhaust gas aftertreatment system. Also included in the diagnostic system (10) is a central diagnostic unit (35) configured to diagnose a condensation condition associated with the sensor (24) for mitigating a sensor failure due to water condensation on the sensor (24), the central diagnostic unit (35) performing the diagnosis on the condensation condition based on water storage and release information related to a component of the exhaust gas aftertreatment system. The sensor (24) is activated based on the water storage and release information.

20 Claims, 7 Drawing Sheets

(56) References Cited

U.S. PATENT DOCUMENTS

| | | | |
|---|---|---|---|
| 9,410,466 B2 | 8/2016 | Surnilla et al. | |
| 9,617,899 B2 * | 4/2017 | Goodwin | F01N 11/00 |
| 10,001,043 B2 * | 6/2018 | Kamp | F02D 41/1494 |
| 2002/0053199 A1 | 5/2002 | Sato et al. | |
| 2003/0043885 A1 | 3/2003 | Yamazaki et al. | |
| 2007/0000235 A1 * | 1/2007 | Ohsaki | F02D 41/1446 |
| | | | 60/274 |
| 2007/0113539 A1 | 5/2007 | Nakano | |
| 2007/0271904 A1 * | 11/2007 | Shouda | F02D 37/02 |
| | | | 60/284 |
| 2010/0300068 A1 * | 12/2010 | Enomoto | F02D 41/1494 |
| | | | 60/273 |
| 2011/0246090 A1 | 10/2011 | Goya | |
| 2012/0260636 A1 | 10/2012 | Hashida et al. | |
| 2012/0304752 A1 | 12/2012 | Krommenhoek et al. | |
| 2016/0290961 A1 | 10/2016 | Aoki et al. | |

FOREIGN PATENT DOCUMENTS

| | | | | |
|---|---|---|---|---|
| CN | 206346813 U | 7/2017 | | |
| DE | 102009024782 A1 | 2/2010 | | |
| DE | 102014209960 A1 | 12/2014 | | |
| EP | 2781893 A1 * | 9/2014 | | F01N 9/005 |
| EP | 2781893 A1 | 9/2014 | | |
| FR | 2934011 A1 | 1/2010 | | |

\* cited by examiner

SYSTEM AND METHOD TO MITIGATE SENSOR FAILURES DUE TO WATER CONDENSATION

CROSS-REFERENCE TO RELATED APPLICATIONS

This application is a national phase filing of International Application No. PCT/IB2017/056259, titled SYSTEM AND METHOD TO MITIGATE SENSOR FAILURES DUE TO WATER CONDENSATION, filed Oct. 10, 2017, the disclosure of which being expressly incorporated herein by reference.

TECHNICAL FIELD

The present disclosure relates generally to systems and methods for diagnosing sensor operation, and more specifically to a diagnostic system and method for diagnosing operation of sensors in an exhaust gas aftertreatment system.

BACKGROUND

Many exhaust systems use a catalyst and a sensor of some kind downstream of the catalyst. In such systems, under certain conditions water may be stored by and released from the catalyst, condensing on the sensor and causing damage. For example, certain diesel aftertreatment systems use a catalyst and a downstream nitrogen oxides (NOx) sensor (e.g., in a vehicle tailpipe) which can be damaged due to water condensation. Catalyst components, especially Zeolite-based catalysts (e.g., Cu-Zeolite catalyst), can store and subsequently release significant amounts of $H_2O$ which can condense on the sensor. The condensation depends on many factors in addition to the engine out $H_2O$ concentration. Therefore, to avoid damage to the sensor, it is typically disabled for a significant time during certain operating conditions that may result in condensation (e.g., during cold start). This approach results in disabling the NOx sensor for longer periods of time than necessary, which results in undesirable periods of time when NOx is not being monitored. This may result in reduced emissions control. Accordingly, there exists a need to control the operational window of such sensors to prevent operation during conditions under which condensation can occur while broadening the operational window.

SUMMARY

According to one embodiment, the present disclosure provides a diagnostic system, including a sensor disposed downstream from an exhaust gas aftertreatment system; and a central diagnostic unit configured to diagnose a condensation condition associated with the sensor for mitigating a sensor failure due to water condensation on the sensor, the central diagnostic unit performing the diagnosis on the condensation condition based on water storage and release information related to a component of the exhaust gas aftertreatment system, such that the sensor is activated based on the water storage and release information.

In one example, the diagnostic system further includes a virtual dew point sensor configured to determine an estimated dew point time and an estimated dew point temperature based on a water release point of the component of the exhaust gas aftertreatment system. In another example, the sensor is activated based on the estimated dew point time and the estimated dew point temperature. In yet another example, the estimated dew point time and the estimated dew point temperature are variable depending on a location of the sensor. In still another example, the water release point is calculated by the central diagnostic unit based on a kinetic model of the water condensation caused by the component of the exhaust gas aftertreatment system. In still yet another example, the kinetic model is a two-site kinetic model having a rate of adsorption and a rate of desorption, both the adsorption and desorption rates associated with the water condensation caused by the component of the exhaust gas aftertreatment system. In a further example, the two-site kinetic model includes a first model associated with the rate of adsorption and a second model associated with the rate of desorption.

In another example, the sensor is a nitrogen oxides sensor. In a further example, the sensor is disposed downstream from a selective catalytic reduction (SCR) catalyst in the exhaust gas aftertreatment system. In a yet further example, the component of the exhaust gas aftertreatment system includes at least one of: an SCR catalyst, a diesel oxidation catalyst, a diesel particulate filter, and an ammonia oxidation catalyst device.

According to another embodiment, the present disclosure provides a diagnostic method for a sensor. The method includes the steps of disposing the sensor downstream from an exhaust gas aftertreatment system; performing a diagnosis on a condensation condition associated with the sensor for mitigating a sensor failure due to water condensation on the sensor; evaluating the condensation condition based on water storage and release information related to a component of the exhaust gas aftertreatment system; and activating the sensor based on the water storage and release information.

In one example, the method includes determining a water release point based on an estimated dew point time and an estimated dew point temperature associated with the component of the exhaust gas aftertreatment system. In a further example, the method includes determining a safe activation point based on the water release point of the component; and activating the sensor based on the safe activation point. In a yet further example, the method includes varying the estimated dew point time and the estimated dew point temperature depending on a location of the sensor. In a still further example, the method includes calculating the water release point based on a kinetic model of the water condensation caused by the component of the exhaust gas aftertreatment system. In a still yet further example, the method includes generating a two-site kinetic model having a rate of adsorption and a rate of desorption, wherein both the adsorption and desorption rates are associated with the water condensation caused by the component of the exhaust gas aftertreatment system. In a variation, the method includes generating a first model associated with the rate of adsorption and a second model associated with the rate of desorption for the two-site kinetic model.

In another example, the method includes including a nitrogen oxides sensor as the sensor. In yet another example, the method includes disposing the sensor downstream from a selective catalytic reduction (SCR) catalyst in the exhaust gas aftertreatment system. In still another example, the method includes including at least one of: an SCR catalyst, a diesel oxidation catalyst, a diesel particulate filter, and an ammonia oxidation catalyst device as the component of the exhaust gas aftertreatment system.

While multiple embodiments are disclosed, still other embodiments of the present disclosure will become apparent to those skilled in the art from the following detailed description, which shows and describes illustrative embodiments of the present disclosure. Accordingly, the drawings and detailed description are to be regarded as illustrative in nature and not restrictive.

BRIEF DESCRIPTION OF THE DRAWINGS

The above-mentioned and other features of this disclosure and the manner of obtaining them will become more apparent and the disclosure itself will be better understood by reference to the following description of embodiments of the present disclosure taken in conjunction with the accompanying drawings, wherein.

Figure 1:
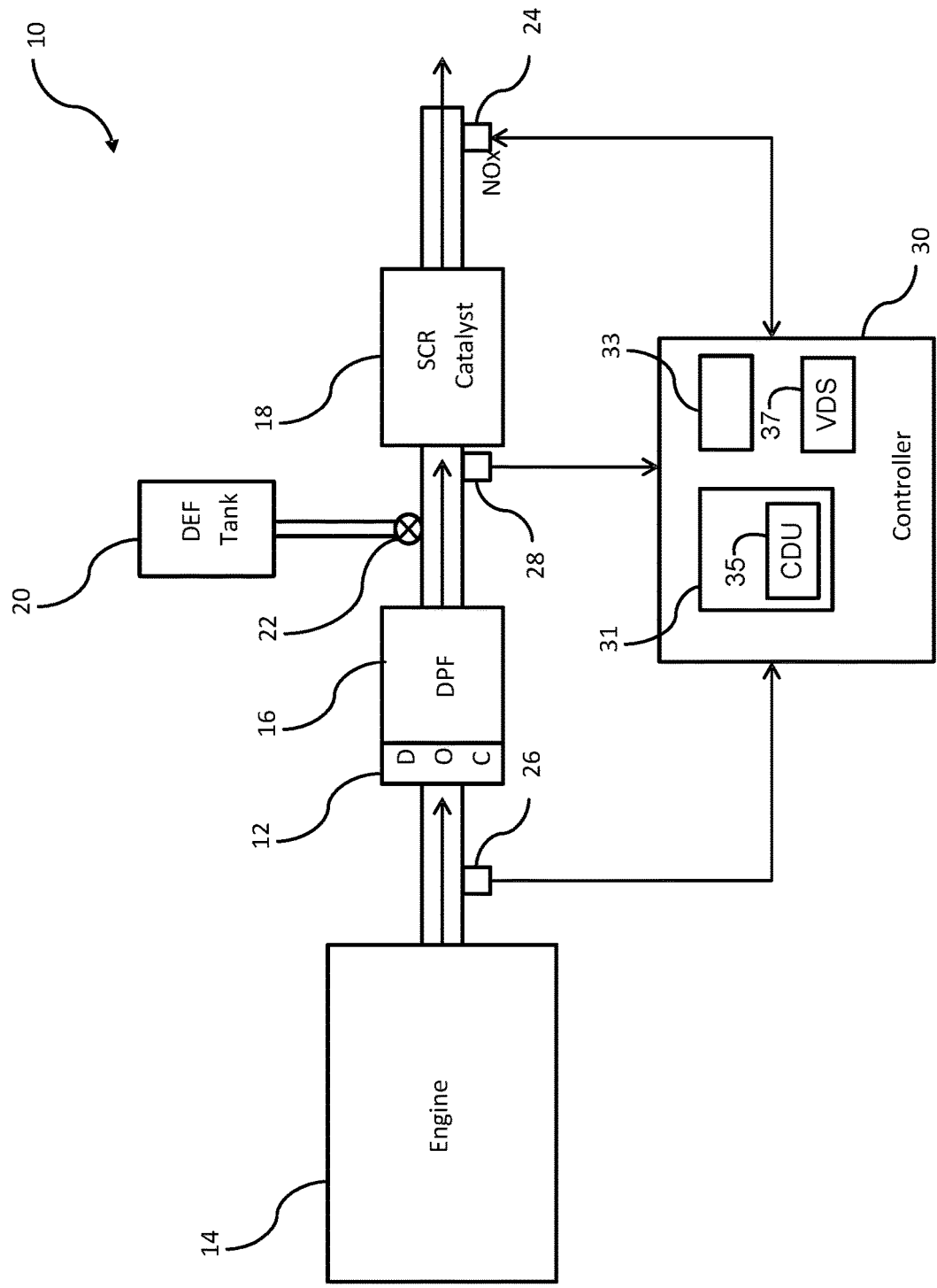
FIG. 1 is a functional block diagram of a sensor diagnostic system, featuring a central diagnostic unit.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

DETAILED DESCRIPTION

Preferred embodiments of the present disclosure are described below by way of example only, with reference to the accompanying drawings. Further, the following description is merely exemplary in nature and is in no way intended to limit the disclosure, its application, or uses. As used herein, the term "unit" or "module" may refer to, be part of, or include an Application Specific Integrated Circuit (ASIC), an electronic circuit, a processor or microprocessor (shared, dedicated, or group) and/or memory (shared, dedicated, or group) that executes one or more software or firmware programs, a combinational logic circuit, and/or other suitable components that provide the described functionality. Thus, while this disclosure includes particular examples and arrangements of the units, the scope of the present safety control system should not be so limited since other modifications will become apparent to the skilled practitioner.

One of ordinary skill in the art will realize that the embodiments provided can be implemented in hardware, software, firmware, and/or a combination thereof. Programming code according to the embodiments can be implemented in any viable programming language such as C, C++, HTML, XTML, JAVA or any other viable high-level programming language, or a combination of a high-level programming language and a lower level programming language.

As used herein, the modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

As is further described below, the present disclosure includes the development of a fundamental model to describe $H_2O$ adsorption and desorption along with thermal effects on catalyst components such as a Cu-Zeolite catalyst. The model is a kinetic model developed from lab data and validated using engine data. The model may be used to predictively determine operational boundaries to mitigate sensor failures due to water condensation. Typical approaches to sensor operation control limit the operational range of the sensor to avoid condensation-induced cracking. Consequently, using such conventional approaches the sensor is disabled for much of the FTP cycle. Using the teachings of the present disclosure, sensor failures due to water condensation may be mitigated while the operational window of the sensor may be broadened compared to conventional methods, thereby enabling compliance with in-use ratio requirements established by the EPA.

Referring now to FIG. 1, a sensor diagnostic system 10 is shown that performs diagnostic processes on one or more sensors of a vehicle (not shown). As shown, system 10 generally includes a diesel oxidation catalyst ("DOC") 12 positioned to receive exhaust from an engine 14, a diesel particulate filter ("DPF") 16 downstream from the DOC 12, a selective catalytic reduction ("SCR") catalyst 18 downstream from the DPF 16, a diesel exhaust fluid ("DEF") tank 20 that supplies DEF to a DEF valve 22 for introduction into the exhaust stream between DPF 16 and SCR catalyst 18, and a NOx sensor 24 downstream from the SCR catalyst 18. System 10 may further include a flow sensor 26 upstream from DOC 12 which indicates the exhaust flow from engine 12 and a temperature sensor 28 positioned to provide an indication of the temperature of exhaust at the inlet of SCR catalyst 18. As is further described herein, an engine control module ("ECM") or controller 30 may be in communication with NOx sensor 24, flow sensor 26 and temperature sensor 28 and configured to carry out an analysis of the operating conditions of system 10 to determine when to activate and deactivate NOx sensor 24.

As shown, controller 30 generally includes a processor 31 and a non-transitory memory 33 having instructions that, in response to execution by processor 31, cause processor 31 to perform the various functions of controller 16 described herein. Processor 31, non-transitory memory 33, and controller 30 are not particularly limited and may, for example, be physically separate. Moreover, in certain embodiments, controller 30 may form a portion of a processing subsystem including one or more computing devices having memory, processing, and communication hardware. Controller 30 may be a single device or a distributed device, and the functions of the controller 30 may be performed by hardware and/or as computer instructions on a non-transient computer readable storage medium, such as non-transitory memory 33.

Included in the processor 31 is a central diagnostic unit ("CDU") 35 configured to diagnose a condensation condition associated with NOx sensor 24 and mitigate a sensor failure due to water condensation on NOx sensor 24 using a virtual dew point sensor ("VDS") 37. In embodiments, CDU 35 is designed to mitigate the sensor failure due to water condensation by determining when it is likely safe to turn on NOx sensor 24. CDU 35 provides, among other things, an approach to controlling NOx sensor operation by using virtual dew point sensor 37 based on a kinetic model. VDS 37 determines operational boundaries of NOx sensor 24 for avoiding potential condensation on the tailpipe NOx sensor 24. Moreover, it is known that idle conditions can also result in water condensation on NOx sensor 24 due to lower temperatures. VDS 37 is also useful to develop strategies during idle conditions to avoid condensation on NOx sensor 24. Thus, it is advantageous that CDU 35 is helpful for increasing the robustness of NOx sensor 24 and broadening its operational window.

While the present disclosure is described primarily in the context of mitigating failures of NOx sensor 24 positioned downstream from SCR catalyst 18, it should be understood that the teachings of the present disclosure may be applied in various other systems. In general, the present disclosure has application to any system having a sensor susceptible to condensation damage positioned downstream of a catalyst that stores water. Other suitable sensors are also contemplated to suit different applications.

In certain embodiments, controller 30 includes one or more interpreters, determiners, evaluators, regulators, and/or processors that functionally execute the operations of controller 30. The description herein including interpreters, determiners, evaluators, regulators, and/or processor emphasizes the structural independence of certain aspects of controller 30, and illustrates one grouping of operations and responsibilities of the controller. Other groupings that execute similar overall operations are understood within the scope of the present application. Interpreters, determiners, evaluators, regulators, and processors may be implemented in hardware and/or as computer instructions on a non-transient computer readable storage medium, and may be distributed across various hardware or computer based components.

Example and non-limiting implementation elements that functionally execute the operations of controller 30 include sensors providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state, any actuator including at least an electrical, hydraulic, or pneumatic actuator, a solenoid, an op-amp, analog control elements (springs, filters, integrators, adders, dividers, gain elements), and/or digital control elements.

Certain operations described herein include operations to interpret and/or to determine one or more parameters or data structures. Interpreting or determining, as utilized herein, includes receiving values by any method known in the art, including at least receiving values from a datalink or network communication, receiving an electronic signal (e.g. a voltage, frequency, current, or PWM signal) indicative of the value, receiving a computer generated parameter indicative of the value, reading the value from a memory location on a non-transient computer readable storage medium, receiving the value as a run-time parameter by any means known in the art, and/or by receiving a value by which the interpreted parameter can be calculated, and/or by referencing a default value that is interpreted to be the parameter value.

As is understood by those skilled in the art, in system 10 exhaust from engine 14 flows through DOC 12 where nitric oxide (NO $O_2$) is converted into $NO_2$. The $NO_2$ reacts with carbon in DPF 16 to produce $CO_2$ and NOx. A mist of DEF is sprayed into the diesel exhaust stream by DEF valve 22 to form ammonia ($NH_3$) through a series of reactions. The NOx and $NH_3$ flow into SCR catalyst 18 where they react to form N and $H_2O$ vapor, thereby reducing the released emissions (NOx and $NH_3$) to near-zero levels.

In the present disclosure, methods and systems are disclosed for predicting water concentration and temperature beyond SCR catalyst 18 (e.g., at NOx sensor 24) by modeling the adsorption and desorption at SCR catalyst 18. As indicated above, SCR catalyst 18 can store significant amounts of water at low temperature, much of which is released with higher temperature, which may cause damaging condensation at NOx sensor 24.

Figure 2:
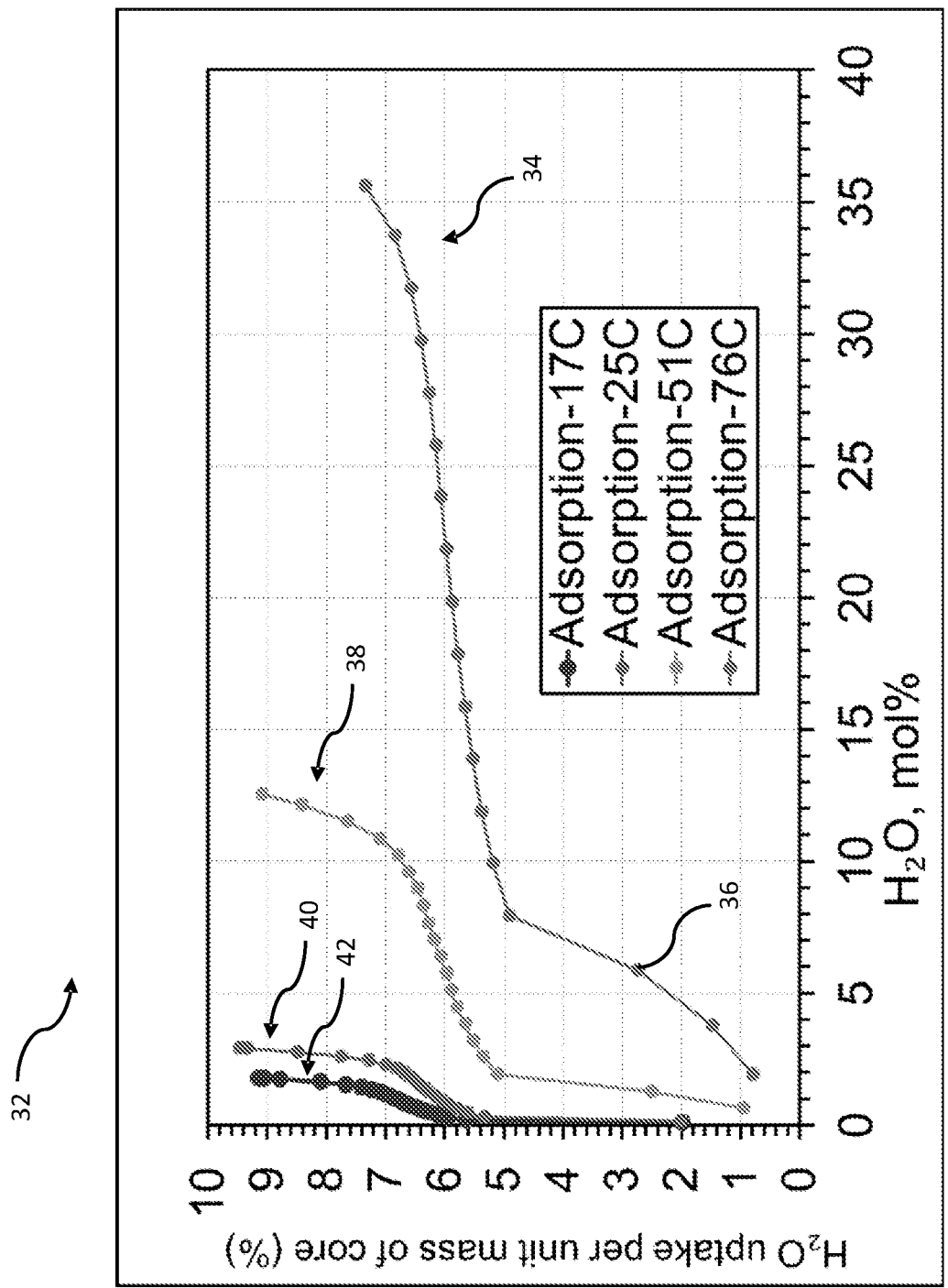
FIGS. 2-7 illustrate exemplary diagnostic methods of the central diagnostic unit of FIG. 1.

Referring now to FIGS. 2-7, exemplary diagnostic methods of CDU 35 using VDS 37 are shown. In FIG. 2, CDU 35 utilizes data shown in a plot 32 depicting the amount of water storage of a catalyst material (such as SCR catalyst 18). Data set 34 of plot 32 shows the water uptake characteristics of the catalyst at a temperature of 76° C. Each point 36 shows the water uptake (Y-axis) after four hours of exposure to the water concentration indicated by the X-axis. For example, as indicated by point 36, it is determined that at 76° C. and a water concentration of approximately 6 mol %, the water uptake of the catalyst is approximately 2.7% per unit mass of the catalyst. This is determined by weighing the sample catalyst when dry (i.e., prior to exposure to the water concentration), and then weighing again after four hours. Data set 38 shows water uptake at a temperature of 51° C. Data set 40 shows water uptake at a temperature of 25° C. Similarly, data set 42 shows water uptake at a temperature of 17° C. As can be seen from the data, the catalyst sample absorbed water much more readily at lower temperatures.

Figure 3:
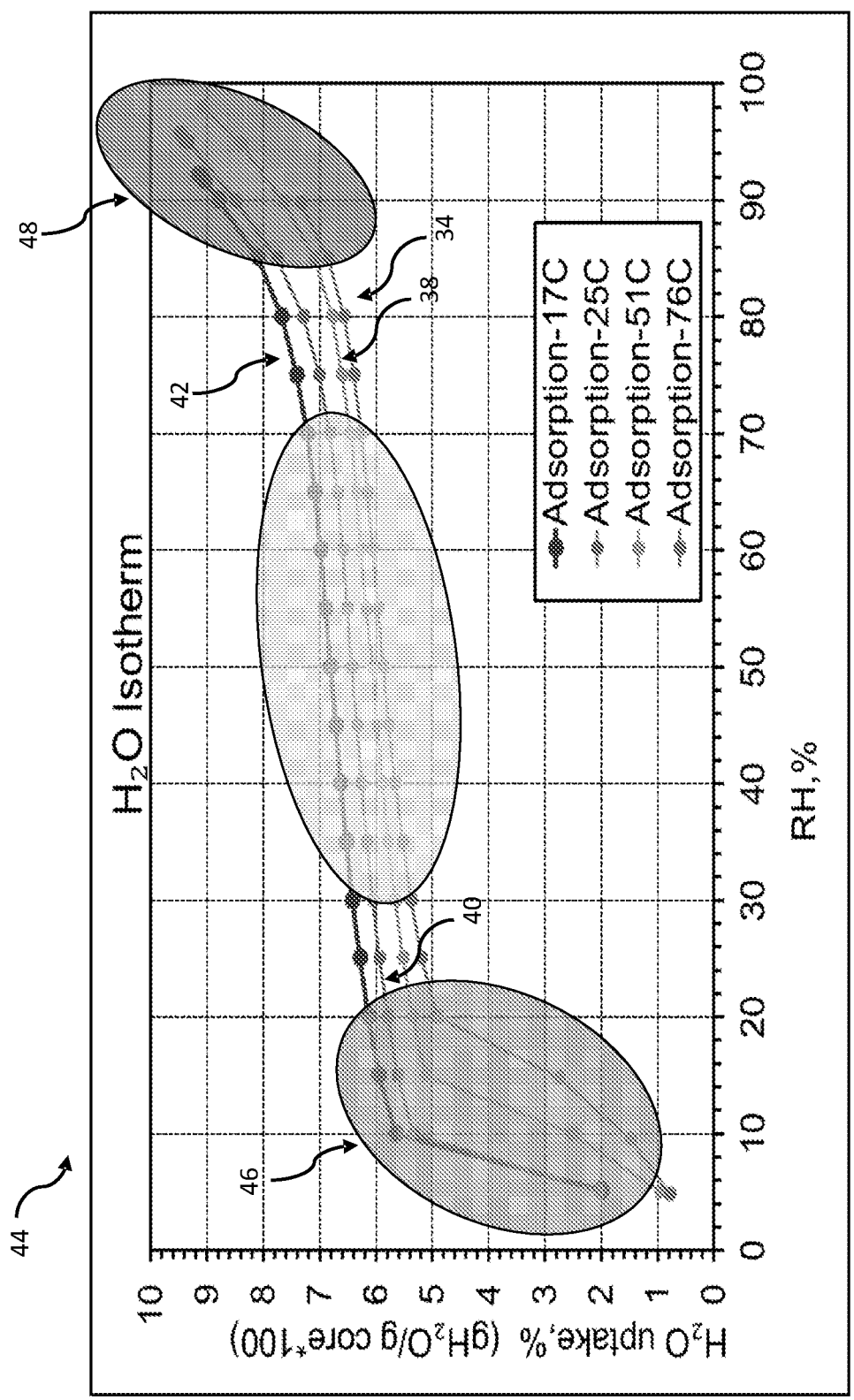

Referring now to FIG. 3, the data depicted in FIG. 2 is reproduced using a different X-axis (e.g., relative humidity percent). As shown in plot 44 of FIG. 3, for all data sets 34, 38, 40, 42 there is a rapid water uptake for water concentrations in region 46. In region 48, actual condensation in the form of water droplets began to occur. For concentrations between regions 46 and 48, water uptake occurred without condensation.

Figure 4:
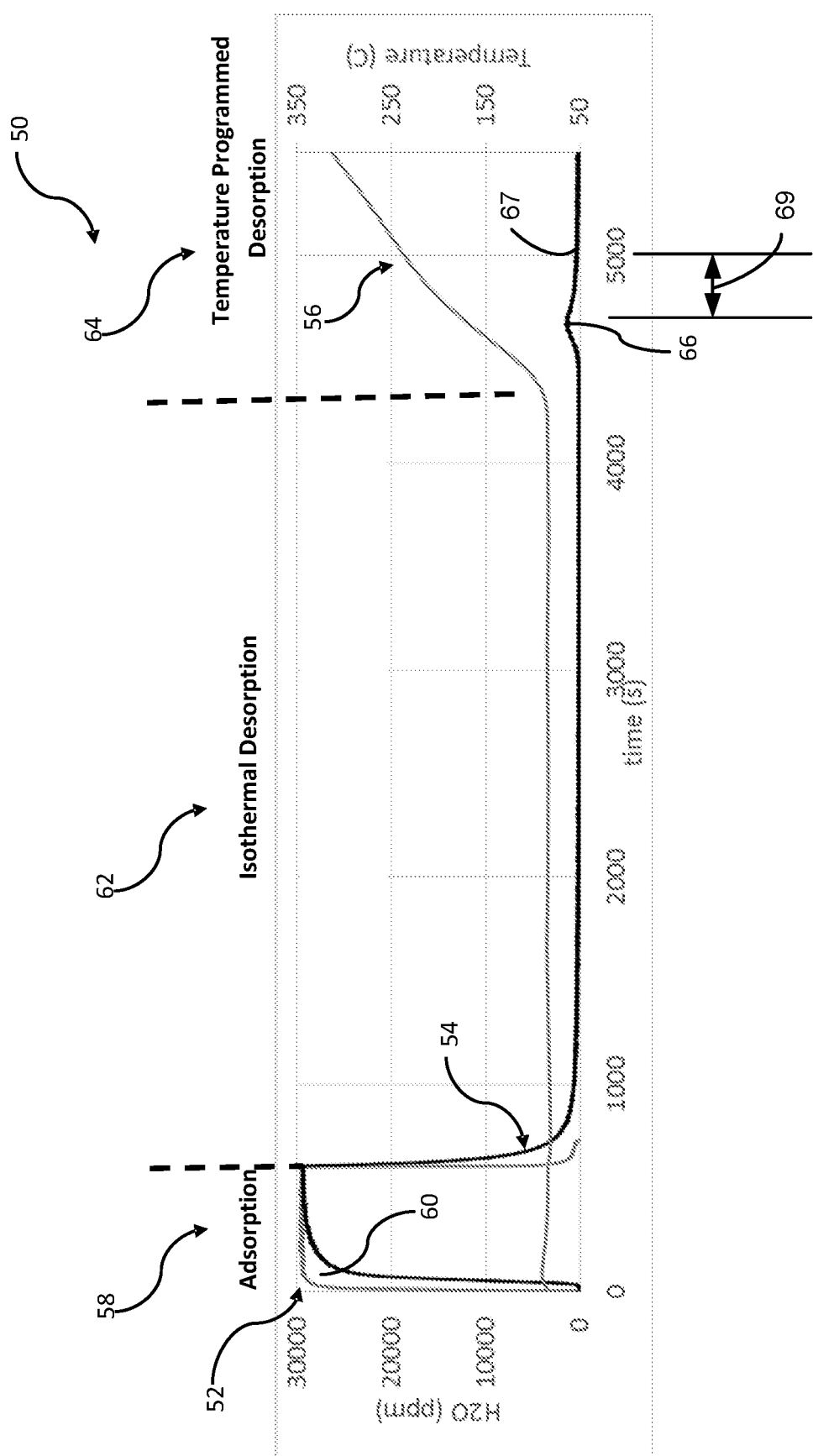

Referring now to FIG. 4, during the diagnostic process, CDU 35 utilizes data shown in a plot 50 depicting the results of an experiment of the dynamics of water storage and release in a sample catalyst. Typically, the sample catalyst is placed in a reactor tube and the gas concentration and temperature provided to the tube is carefully controlled. Plot 50 includes water concentration of an inlet gas 52, water concentration 54 of the sample catalyst and temperature 56. During the adsorption phase of the experiment (indicated by region 58 encompassing approximately the first 600 seconds), temperature is held constant at approximately 80° C. and gas having a water concentration of approximately 3% is supplied to the reactor tube.

In certain cases, SCR catalyst 18 can store significant amount of water at low temperature. At higher temperatures, the water can be released as vapor. Even though engine out $H_2O$ concentration may not exceed a dew point level, the additional water vapor released by aftertreatment system components can exceed the dew point level at the sensor location (which could be cooler than the catalyst surface) and hence condense out the water and damage NOx sensor 24. If engine out water is at 10%, the vapor release will add to the water condensation, increasing the water concentration to 15%. This can exceed the dew point level and lead to condensation. Conventional diagnostic systems do not address this additional stored water in the aftertreatment system components, such as SCR catalyst 18, DOC 12, DPF 16, AMOX (ammonia oxidation catalyst devices), or the like. For example, SCR catalyst 18 stores a maximum amount of water that is up to 4 or 5 times more than that of DOC 12.

When water is stored on SCR catalyst 18, it is an exothermic process leading to significant heat rise. For example, an SCR out temperature can be higher than SCR in temperature. During water release, the opposite happens. SCR out temperature is less than SCR in temperature. Further, there is added water from SCR catalyst 18. These two factors are especially conducive to water condensation on NOx sensor 24. In some cases, a temperature drop can be as much as 70° Celsius (C) across two ends of SRC catalyst 18. For example, if the temperature drop is another 20° C. at the tailpipe, this is a significant drop in temperature that can lead to condensation.

As shown, sample water concentration 54 lagged inlet gas concentration 52, and an area 60 between sample water concentration 54 and inlet gas concentration 52 represents the water that is stored in the sample catalyst. Specifically, the sample catalyst is saturated at the end of adsorption region 58. During the isothermal desorption region 62, the inlet gas is switched off and the temperature is held at approximately 80° C. for approximately one hour. During the temperature programmed desorption phase of the experiment (indicated by region 64) thermal desorption spectroscopy is used to observe desorbed molecules from the surface of the sample catalyst as temperature 56 is increased. As shown, as temperature 56 is ramped through approximately 150° C., a small amount of water is released at a water release point 66 (see an increase in sample water concentration 54) demonstrating that a portion of the adsorbed water requires a higher temperature for release.

VDS 37 is configured to determine an estimated dew point time and an estimated dew point temperature based on the water release point 66. The estimated dew point time and the estimated dew point temperature are variable depending on a location of NOx sensor 24. In embodiments, if the exhaust gas temperature is below the estimated dew point temperature, CDU 35 places NOx sensor 24 in a deactivated state (e.g., turn it off if already turned on) during cold idle, start-up time, cold ambient, cold start, etc. As such, CDU 35 provides the ability to model the storage and release of water on the catalyst surface. Conventional sensor diagnostic systems do not take into account the water storage and release on the aftertreatment system components.

In embodiments, CDU 35 determines a safe activation point 67 by adding a predetermined time period 69 to the water release point 66, such that NOx sensor 24 is activated immediately after the water condensation associated with NOx sensor 24 is less than a predetermined threshold. As a result, NOx sensor 24 is activated faster and earlier than conventional systems and thus CDU 35 provides enhanced NOx emission control. In conventional systems, NOx sensor 24 is typically deactivated for a longer time period during most of the cold start period because the water release point 66 at the location of NOx sensor 24 is unknown. In contrast, with CDU 35, NOx sensor 24 is activated earlier, causing fuel efficiency benefits, and EPA in-use ratio requirements are met faster since CDU 35 activates NOx sensor 24 earlier. As a result, an operating window of NOx sensor 24 is broadened.

Figure 6:
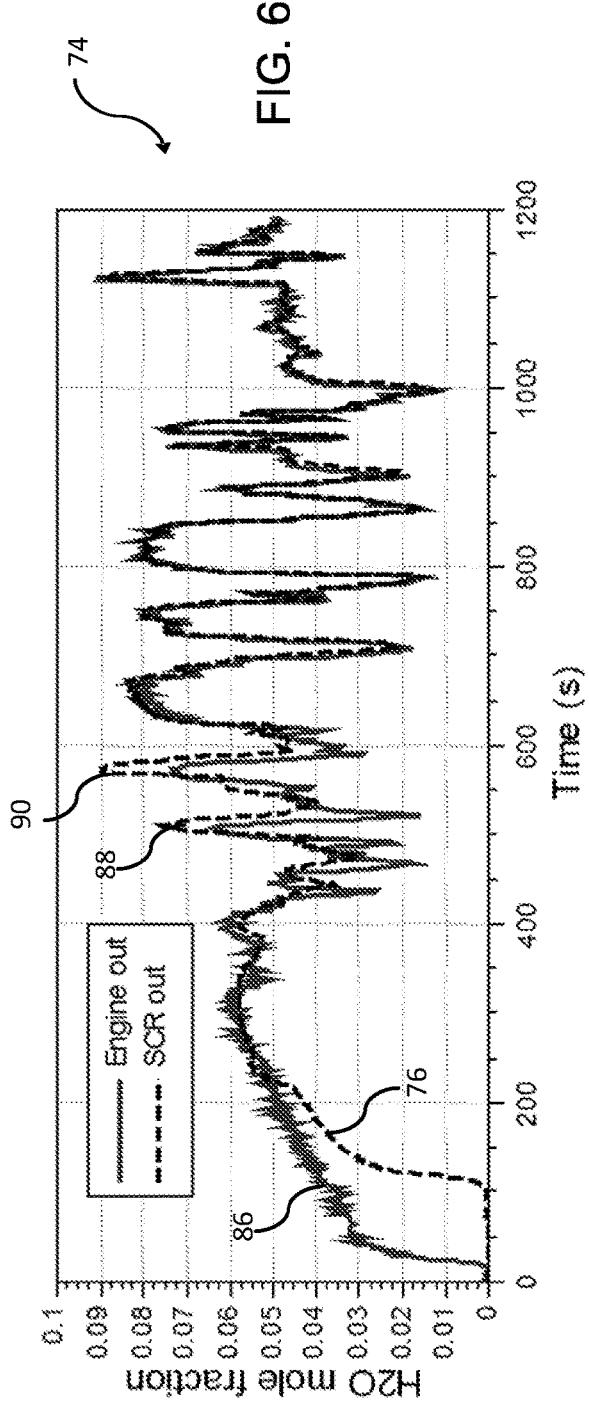

For example, NOx sensor 24 is turned on based on dew point prediction which requires knowledge of water concentration and temperature at the location of NOx sensor 24. In a conventional system, the water concentration is obtained from exhaust. However, as shown in FIG. 6, water concentration at SCR 18 outlet can be higher than exhaust due to a release of stored water (see spikes 88, 90 in FIG. 6). This phenomenon is described in further detail below. CDU 35 accurately predicts the dew point based on the water storage effect on catalytic components of the aftertreatment system.

Figure 5:
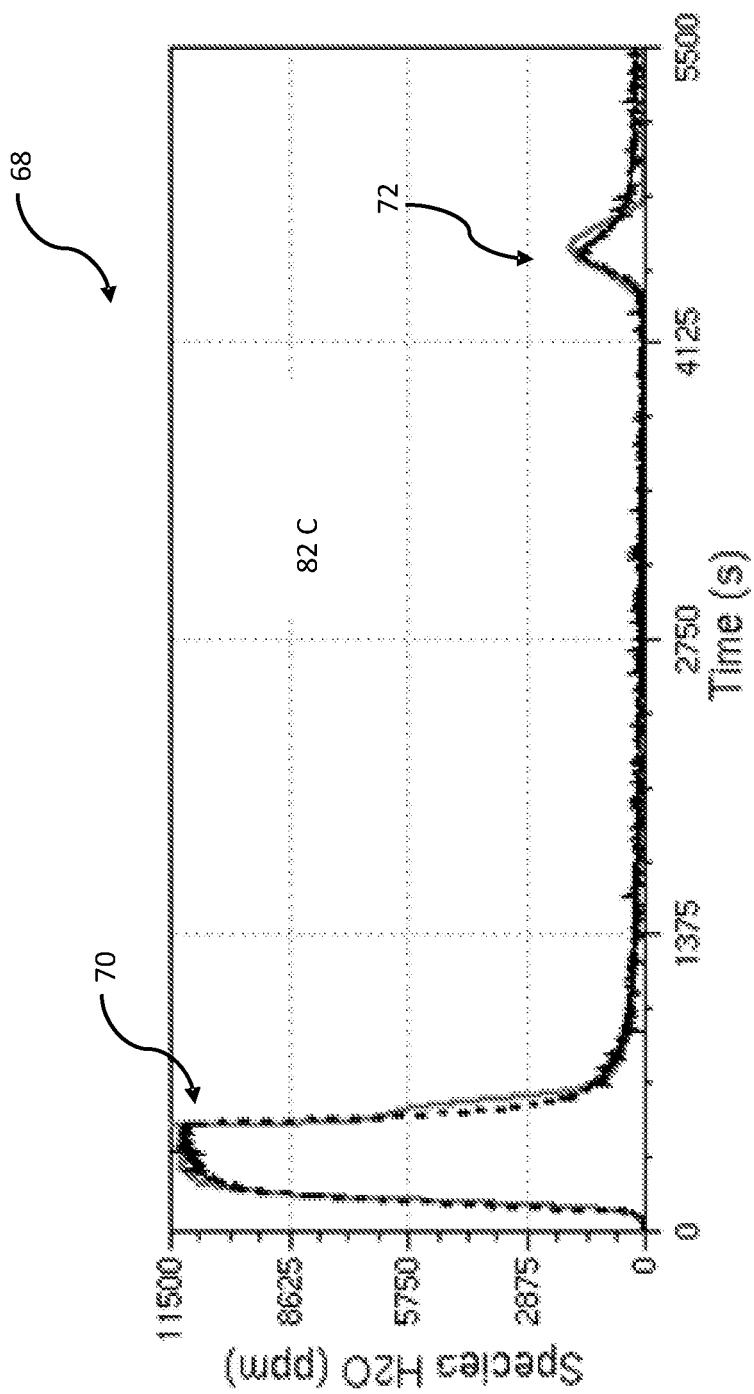

Referring now to FIGS. 4 and 5, CDU 35 generates a plot 68 of a two-site kinetic model of water concentration of a catalyst exposed to gas having approximately 1% water concentration over time at approximately 82° C. More specifically, plot 68 shows results 70 of a first model of weakly bound water and results 72 of a second model of strongly bound water.

For each model component, the following rate expressions are used: rate of adsorption=$k_{ads}C_{H2O}(1-\theta)$ and rate of desorption=$k_{des}\theta$; where $$k_{des} = A_{des}\exp\left[\frac{-E_{des}}{RT}(1-\alpha\theta)\right].$$

For the weakly bound model, $E_{des}$=54 kJ/mol; $A_{des}$=6.6e11; and $\alpha$=0. For the strongly bound model, $E_{des}$=100 kJ/mol; $A_{des}$=2.04e13; and $\alpha$=0.13. Theta is dimensionless water stored on the catalyst compared to its capacity to store water. As should be apparent from the foregoing, when theta is one, the catalyst is saturated (i.e., no more adsorption can occur). $K_{ads}$ is the rate constant for adsorption, which is independent of temperature. $K_{des}$ is the rate constant for desorption, which is a strong function of temperature. In embodiments, weakly bound water is desorbed at a lower temperature. For example, primarily weakly bound water is desorbed during isothermal desorption, as shown in region 62 of FIG. 4. However, strongly bound water is primarily desorbed at a higher temperature, as shown in region 64 of FIG. 4. Using the above-described model, the water concentration and temperature can be predicted at the location of outlet of SCR catalyst 18. In some embodiments, there is a heat loss between the outlet of SCR catalyst 18 and the location of NOx sensor 24. Therefore, the temperature and concentration at the location of NOx sensor 24 can be predicted using an empirical model based on actual measurements. For example, the first model 70 corresponds to the end of adsorption region 58 shown in FIG. 4, and the second model 72 corresponds to the water release point 66 shown in FIG. 4.

Figure 7:
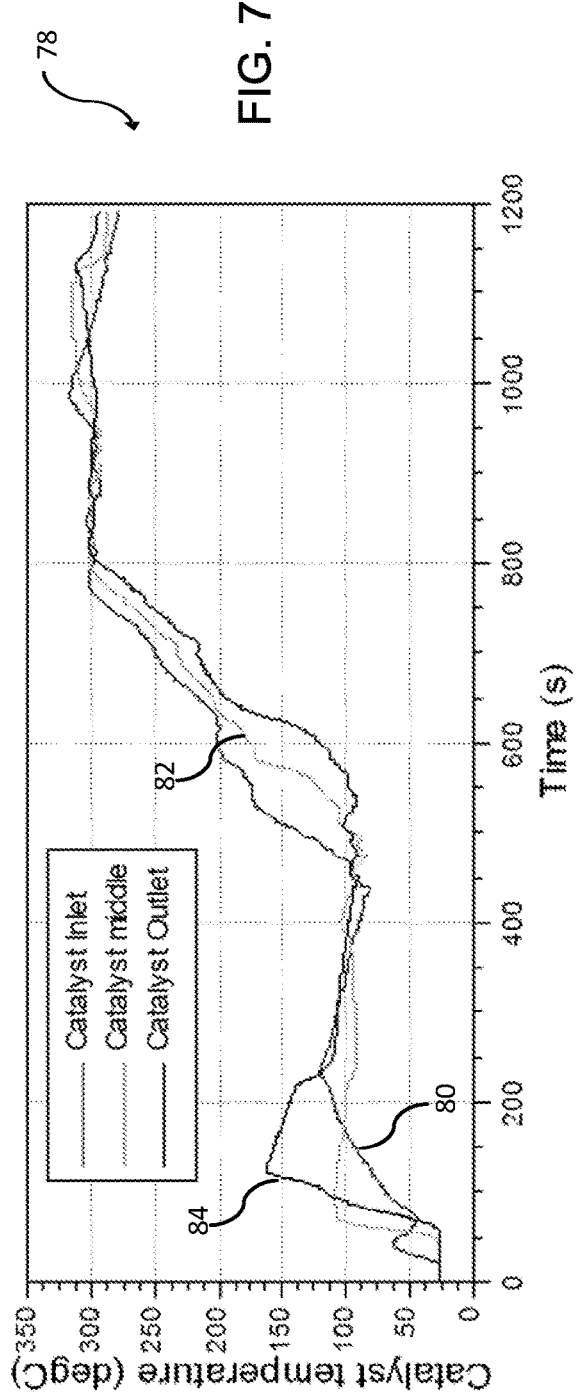

Referring now to FIGS. 6 and 7, CDU 35 generates a graph 74 of water concentration during a typical cold start FTP regulatory cycle. During the cold start period (i.e., approximately 0 to 200 seconds), a significant amount water is stored on SCR catalyst 18 as shown by dotted line 76 of FIG. 6. This water storage is accompanied by a large heat release. As a result, the temperature increases sharply along the length of SCR catalyst 18 (see plot 78 of FIG. 7 showing simulated catalyst inlet temperature 80, catalyst middle temperature 82 and catalyst outlet temperature 84). Finally, when SCR catalyst 18 is sufficiently warm (e.g., beyond 500 seconds), the stored water is released creating spikes in water concentration of SCR catalyst 18 as shown by dotted line 76 that are beyond engine out water concentration 86 (e.g., see spikes 88, 90). These spikes can exceed dew point levels in the vicinity of NOx sensor 24, depending on the temperature at the sensor location. That temperature is influenced not only by the engine-out heat propagation through the system, but also by the heat effects of $H_2O$ storage and release.

Figure 8:
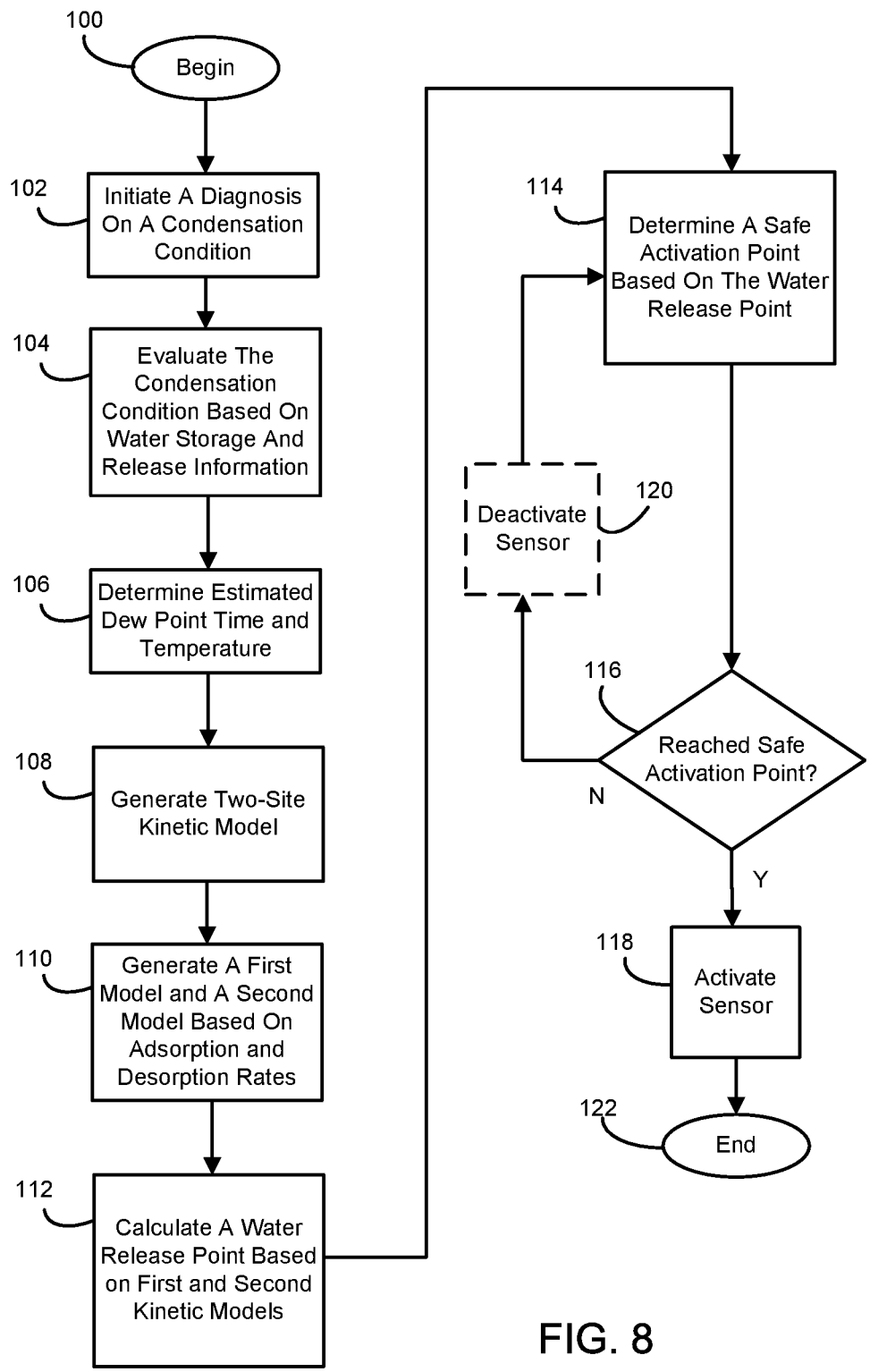
FIG. 8 is a flow chart of an exemplary method of executing the diagnostic methods of the central diagnostic unit of FIG. 1.

Referring now to FIG. 8, an exemplary method or process of executing diagnostic system 10 is illustrated. Although the following steps are primarily described with respect to the embodiments of FIGS. 1-7, it should be understood that the steps within the methods can be modified and executed in a different order or sequence without altering the principles of the present disclosure.

The method begins at step 100. In step 102, CDU 35 initiates a diagnosis on a condensation condition associated with NOx sensor 24 for mitigating a sensor failure due to water condensation on NOx sensor 24. In step 104, CDU 35 evaluates the condensation condition based on water storage and release information related to SCR catalyst 18. As discussed above, the water storage and release information is used to activate NOx sensor 24 during the cold start period. In step 106, VDS 37 determines an estimated dew point time and an estimated dew point temperature based on a water release point of the sample catalyst in SCR catalyst 18. However, the estimated dew point time and the estimated dew point temperature vary depending on a location of NOx sensor 24. It is also contemplated that the location of NOx sensor 24 is variable depending on the application. For example, NOx sensor 24 is located downstream from AMOX or engine 14. Other suitable configurations are contemplated to suit different applications.

In step 108, CDU 35 generates a two-site kinetic model having a rate of adsorption and a rate of desorption. Both the adsorption and desorption rates are associated with the water condensation caused by the sample catalyst in SCR catalyst 18. In step 110, CDU 35 generates a first kinetic model associated with the rate of adsorption and a second kinetic model associated with the rate of desorption for the two-site kinetic model. In step 112, CDU 35 calculates the water release point 66 based on the first and second kinetic models of the water condensation caused by the sample catalyst in SCR catalyst 18. In step 114, CDU 35 determines a safe activation point 67 by adding the predetermined time period 69 to the water release point 66, such that NOx sensor 24 is activated immediately after the water condensation associated with NOx sensor 24 is less than a predetermined threshold.

In step 116, when the safe activation point 67 is reached in time and temperature, control proceeds to step 118. Otherwise, control proceeds to step 120. In step 118, NOx sensor 24 is activated, e.g., by CDU 35. In step 120, if NOx sensor 24 is in an activated state, NOx sensor 24 is deactivated, e.g., by CDU 35. However, if NOx sensor 24 is already in a deactivated state, step 120 is an optional step and no deactivation is performed. In some embodiments, if NOx sensor 24 is in the deactivated state, CDU 35 prevents NOx sensor 24 from being activated until the safe activation point 67 is reached. It is also contemplated that NOx sensor 24 is activated based on the estimated dew point time and the estimated dew point temperature. The method ends at step 122 which may include a return to step 102.

It should be further understood that, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

While the present disclosure has been described as having exemplary designs, the present disclosure can be further modified within the spirit and scope of this disclosure. This application is therefore intended to cover any variations, uses, or adaptations of the present disclosure using its general principles. Further, this application is intended to cover such departures from the present disclosure as come within known or customary practice in the art to which this present disclosure pertains and which fall within the limits of the appended claims.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A diagnostic system, comprising:
 a sensor disposed downstream from an exhaust gas aftertreatment system; and
 a central diagnostic unit configured to diagnose a condensation condition associated with the sensor for mitigating a sensor failure due to water condensation on the sensor, the central diagnostic unit performing the diagnosis on the condensation condition based on water storage and release information related to a catalyst material of a component of the exhaust gas aftertreatment system, such that the sensor is activated based on the water storage and release information.

2. The diagnostic system of claim 1, further comprising a virtual dew point sensor configured to determine an estimated dew point time and an estimated dew point temperature based on a water release point of the component of the exhaust gas aftertreatment system.

3. The diagnostic system of claim 2, wherein the sensor is activated based on the estimated dew point time and the estimated dew point temperature.

4. The diagnostic system of claim 2, wherein the estimated dew point time and the estimated dew point temperature are variable depending on a location of the sensor.

5. The diagnostic system of claim 2, wherein the water release point is calculated by the central diagnostic unit based on a kinetic model of the water condensation caused by the component of the exhaust gas aftertreatment system.

6. The diagnostic system of claim 5, wherein the kinetic model is a two-site kinetic model having a rate of adsorption and a rate of desorption, both the adsorption and desorption rates associated with the water condensation caused by the component of the exhaust gas aftertreatment system.

7. The diagnostic system of claim 6, wherein the two-site kinetic model includes a first model associated with the rate of adsorption and a second model associated with the rate of desorption.

8. The diagnostic system of claim 1, wherein the sensor is a nitrogen oxides sensor.

9. The diagnostic system of claim 1, wherein the sensor is disposed downstream from a selective catalytic reduction (SCR) catalyst in the exhaust gas aftertreatment system.

10. The diagnostic system of claim 1, wherein the component of the exhaust gas aftertreatment system includes at least one of: an SCR catalyst, a diesel oxidation catalyst, a diesel particulate filter, and an ammonia oxidation catalyst device.

11. A diagnostic method for a sensor, comprising:
disposing the sensor downstream from an exhaust gas aftertreatment system;
performing a diagnosis on a condensation condition associated with the sensor for mitigating a sensor failure due to water condensation on the sensor;
evaluating the condensation condition based on water storage and release information related to a catalyst material of a component of the exhaust gas aftertreatment system; and
activating the sensor based on the water storage and release information.

12. The diagnostic method of claim 11, further comprising determining a water release point based on an estimated dew point time and an estimated dew point temperature associated with the component of the exhaust gas aftertreatment system.

13. The diagnostic method of claim 12, further comprising determining a safe activation point based on the water release point of the component; and activating the sensor based on the safe activation point.

14. The diagnostic method of claim 12, further comprising varying the estimated dew point time and the estimated dew point temperature depending on a location of the sensor.

15. The diagnostic method of claim 12, further comprising calculating the water release point based on a kinetic model of the water condensation caused by the component of the exhaust gas aftertreatment system.

16. The diagnostic method of claim 15, further comprising generating a two-site kinetic model having a rate of adsorption and a rate of desorption, wherein both the adsorption and desorption rates are associated with the water condensation caused by the component of the exhaust gas aftertreatment system.

17. The diagnostic method of claim 16, further comprising generating a first model associated with the rate of adsorption and a second model associated with the rate of desorption for the two-site kinetic model.

18. The diagnostic method of claim 11, further comprising including a nitrogen oxides sensor as the sensor.

19. The diagnostic method of claim 11, further comprising disposing the sensor downstream from a selective catalytic reduction catalyst in the exhaust gas aftertreatment system.

20. The diagnostic method of claim 11, further comprising including at least one of: an SCR catalyst, a diesel oxidation catalyst, a diesel particulate filter, and an ammonia oxidation catalyst device as the component of the exhaust gas aftertreatment system.

* * * * *